United States Patent
Cruz (10) Patent No.: US 10,926,103 B2
(45) Date of Patent: Feb. 23, 2021

(54) ENERGY DEGRADER HAVING LAYER STRUCTURE PARALLEL TO THE INCIDENT BEAM DIRECTION FOR RADIATION THERAPY SYSTEM

(71) Applicant: Varian Medical Systems, Inc., Palo Alto, CA (US)

(72) Inventor: Luis Alberto Cruz, Miami, FL (US)

(73) Assignee: Varian Medical Systems, Inc., Palo Palo, CA (US)

( * ) Notice: Subject to any disclaimer, the term of this patent is extended or adjusted under 35 U.S.C. 154(b) by 322 days.

(21) Appl. No.: 15/457,561

(22) Filed: Mar. 13, 2017

(65) Prior Publication Data

US 2017/0182336 A1    Jun. 29, 2017

Related U.S. Application Data

(62) Division of application No. 14/040,345, filed on Sep. 27, 2013.

(Continued)

(51) Int. Cl.
*G21K 1/06* (2006.01)
*G21K 1/10* (2006.01)
(Continued)

(52) U.S. Cl.
CPC .......... *A61N 5/10* (2013.01); *A61N 5/1081* (2013.01); *D21H 19/66* (2013.01);
(Continued)

(58) Field of Classification Search
None
See application file for complete search history.

(56) References Cited

U.S. PATENT DOCUMENTS

| | | | |
|---|---|---|---|
| 4,300,055 A | * | 11/1981 | Taumann ........... H01J 35/00 378/158 |
| 5,440,133 A | | 8/1995 | Moyers et al. |

(Continued)

FOREIGN PATENT DOCUMENTS

| | | |
|---|---|---|
| CN | 1189383 | 8/1998 |
| CN | 101120428 | 2/2008 |

(Continued)

OTHER PUBLICATIONS

R. Svensson, B. Lind and A. Brahme, "Beam characteristics and clinical possibilities of a new compact treatment unit design combining narrow pencil beam scanning and segmental multileaf collimation," Med. Phys. 25: 2358-2369 (1998) (Year: 1998).*

*Primary Examiner* — James Choi (57) ABSTRACT

An energy degrading device for attenuating energy of a particle beam with reduced emittance growth. An energy degrader comprises an emittance control material that can preferentially scatter the beam particles that is incident on a surface with a shallow angle. In one approach, the energy degrader may include alternating layers of a low-Z and a high-Z material, wherein the low Z material serves to attenuate energy of the beam particles by virtue of scattering and the high Z material serves to suppress the emittance increase by scattering back the beam particles toward the beam axis. In another approach, the energy degrader may be composed of carbon nanotubes or a material with oriented crystalline structure that is substantially orientated in the incident direction of the particle beam. The carbon nanotubes may serve to preferentially scatter beam particles towards the central beam axis as well as attenuate energy thereof.

9 Claims, 8 Drawing Sheets

Related U.S. Application Data (60) Provisional application No. 61/793,857, filed on Mar. 15, 2013.

(51) Int. Cl.
    *A61N 5/10* (2006.01)
    *D21H 27/00* (2006.01)
    *D21H 19/66* (2006.01)

(52) U.S. Cl.
    CPC ........... *D21H 27/002* (2013.01); *G21K 1/062* (2013.01); *G21K 1/10* (2013.01); *A61N 2005/109* (2013.01); *A61N 2005/1087* (2013.01); *A61N 2005/1089* (2013.01); *A61N 2005/1095* (2013.01); *Y10T 428/24802* (2015.01)

(56) References Cited

U.S. PATENT DOCUMENTS

| | | | |
|---|---|---|---|
| 5,854,490 A * | 12/1998 | Ooaeh | H01J 37/065 250/492.23 |
| 6,757,355 B1 * | 6/2004 | Siochi | A61N 5/1042 378/147 |
| 2001/0016027 A1 | 8/2001 | Dismore | |
| 2003/0160189 A1 * | 8/2003 | Matsuda | G21K 5/04 250/492.3 |
| 2004/0062353 A1 * | 4/2004 | Kato | A61N 5/1042 378/152 |
| 2006/0017015 A1 | 1/2006 | Sliski et al. | |
| 2008/0189859 A1 * | 8/2008 | Sloan | A61N 5/10 5/601 |
| 2009/0296885 A1 | 12/2009 | Boeh et al. | |
| 2010/0034357 A1 * | 2/2010 | Svesson | A61N 5/1042 378/152 |
| 2010/0051833 A1 * | 3/2010 | Guertin | H05H 7/12 250/515.1 |
| 2010/0230620 A1 | 9/2010 | Tsoupas et al. | |
| 2010/0264327 A1 * | 10/2010 | Bonig | G21K 1/10 250/396 R |
| 2010/0308235 A1 | 12/2010 | Sliski et al. | |
| 2011/0303858 A1 | 12/2011 | Bert et al. | |
| 2012/0267544 A1 | 10/2012 | Ueda | |
| 2013/0032731 A1 | 2/2013 | Tombrello, Jr. et al. | |
| 2014/0005463 A1 | 1/2014 | Jongen | |

FOREIGN PATENT DOCUMENTS

| | | | |
|---|---|---|---|
| CN | 102596316 | 7/2012 | |
| CN | 102695544 | 9/2012 | |
| CN | 102763169 | 10/2012 | |
| CN | 102782799 | 11/2012 | |
| EP | 2327449 | 1/2011 | |
| JP | H08280823 | 10/1996 | |
| JP | H08511978 | 12/1996 | |
| JP | 2003255093 | 9/2003 | |
| JP | 2004049884 | 2/2004 | |
| JP | 2007534391 | 11/2007 | |
| WO | WO-2005004168 A1 * | 1/2005 | ........... A61N 5/1042 |

* cited by examiner

ENERGY DEGRADER HAVING LAYER STRUCTURE PARALLEL TO THE INCIDENT BEAM DIRECTION FOR RADIATION THERAPY SYSTEM

CROSS REFERENCE

This application is a divisional application of the co-pending U.S. patent application Ser. No. 14/040,345, entitled "ENERGY DEGRADER FOR RADIATION THERAPY SYSTEM," filed on Sep. 27, 2013, which claims the benefit and priority to U.S. provisional application No. No. 61/793, 857, filed on Mar. 15, 2013, titled "HIGH EFFICIENCY DEGRADER FOR RADIATION ENERGY SELECTION SYSTEM". The foregoing patent applications are hereby incorporated by reference in entirety for all purposes.

TECHNICAL FIELD

Embodiments of the present disclosure relate generally to medical devices, and more particularly, to radiation therapy devices.

BACKGROUND

In a typical proton therapy system used for tumor radiation treatments for example, a proton beam can be produced in an accelerator, e.g., cyclotron or a synchrotron, in a fixed level of energy that can be then adjusted to a prescribed energy level through energy degradation and energy selection. An energy degrader disposed in vicinity of the accelerator is commonly used to decrease energy of the proton beam. For instance, a cyclotron can produce a proton beam of 250 MeV protons with an emittance of roughly 4 Pi-mm-mRad. An energy degrader may be used to decrease the energy from 250 MeV to 70 MeV in steps of 0.1 MeV for example.

Due to particle scattering between the beam particle and energy degrader material, the beam exiting the energy degrader typically has energy spread centered around the desired final beam energy and direction variations that reduce the quality of the final treatment beam. In other words, the energy degrader causes emittance increase of the beam.

Figure 1:
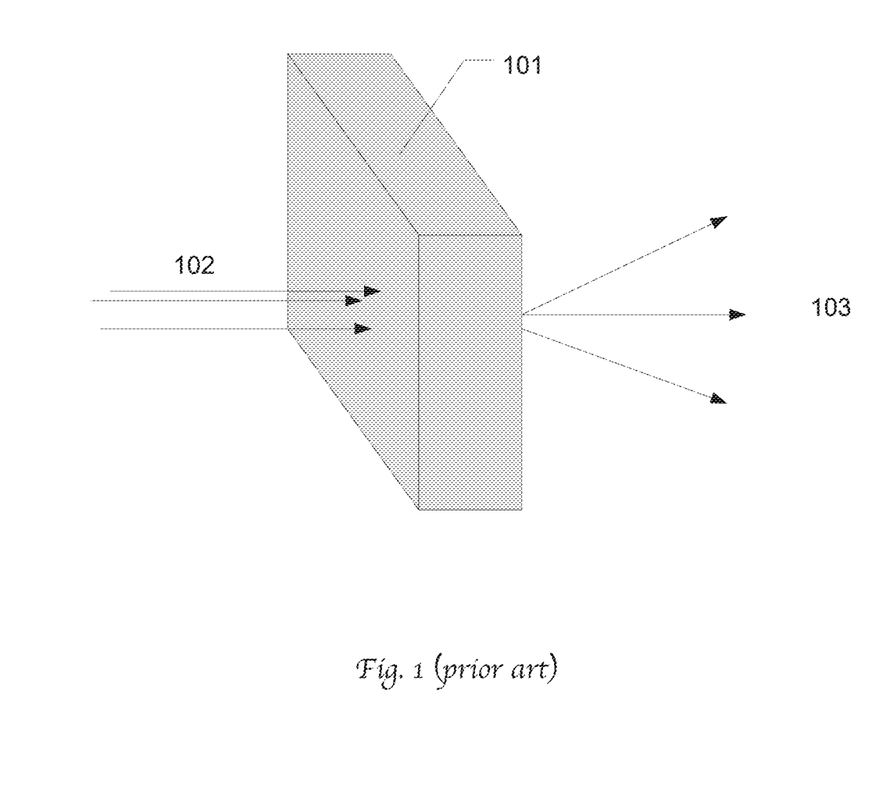
FIG. 1 is a diagram illustrating the particle emittance growth caused by particle scattering within an energy degrader in accordance with the prior art.

Conventionally, the energy degrader is composed of a material with a low atomic number. FIG. 1 is a diagram illustrating the particle emittance growth caused by particle scattering within an energy degrader 101 in accordance with the prior art. The energy degrader may be made of a block of graphite, e.g., with 6 constituent wedges (not explicitly shown) such that the exiting beam energy can be varied by adjusting the positions of the wedges and thus thickness of material that the beam transmits through. As shown, as an incident proton beam 102 passes the energy degrader 101, scattering of the beam 102 occurs in the graphite 101 and results in a large increase in spatial emittance as the beam 103 exists the energy degrader. In other words, the beam 102 becomes a broader beam 103 that has energy-range shifted and spatially scattered.

Because the downstream beam transportation line usually has limited emittance acceptance, the scattered beam is collimated and thereby only a fraction of the initial beam extracted from an accelerator can be transported for downstream radiation use. The emittance growth caused by the energy degrader and the associated collimation by an energy selection system (ESS) undesirably result in very low beam transmission efficiency of the ESS, especially when energy degrader is configured to attenuate the beam to a low level, e.g., 1%.

SUMMARY OF THE INVENTION

Therefore, it would be advantageous to provide a mechanism to degrade energy of a particle beam without causing significant emittance growth.

Accordingly, embodiments of the present disclosure employ an energy degrader comprising an emittance control material that can preferentially scatter the beam particles that is incident on the material surface with a shallow angle. In one approach, the energy degrader may include alternating layers of a low-Z and a high-Z material, wherein Z represents atomic or molecular weight of a material. The low-Z material serves to attenuate energy of the beam particles by virtue of scattering and the high-Z material serves to suppress the emittance increase by scattering back the beam particles toward the beam axis. The low Z material may be selected from Lucite, graphite, carbon, aluminum, lithium, water, and etc. The high Z material may be selected from Tungsten, Lead, Tantalum, and etc. In another approach, the energy degrader may comprise carbon nanotubes or other material having a crystalline structure that is substantially orientated in an incident direction of the particle beam. The carbon nanotubes may serve to preferentially scatter beam particles towards the central beam axis as well as attenuate energy thereof. Therefore, the particle beam can exit the energy degrader in reduced emittance growth which can advantageously improve the energy selection system transmission efficiency.

In one embodiment of the present disclosure, a radiation therapy system comprises an accelerator operable to generate a particle beam, and an energy degrader operable to attenuate energy of the particle beam by virtue of particle scattering, wherein the particle scattering causes spatial emittance growth of the particle beam, wherein the energy degrader comprises a first material operable to constrain the spatial emittance growth by virtue of particle interactions. The degrader may comprise a second material operable to attenuate energy of the particle beam by the particle scattering, and wherein the first material and the second material have substantially different atomic or molecular weights. The energy degrader may also comprise carbon nanotubes oriented approximately in an incident direction of the particle beam.

The foregoing is a summary and thus contains, by necessity, simplifications, generalizations and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

Embodiments of the present invention will be better understood from a reading of the following detailed description, taken in conjunction with the accompanying drawing figures in which like reference characters designate like elements and in which.

DETAILED DESCRIPTION

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail so as not to unnecessarily obscure aspects of the embodiments of the present invention. Although a method may be depicted as a sequence of numbered steps for clarity, the numbering does not necessarily dictate the order of the steps. It should be understood that some of the steps may be skipped, performed in parallel, or performed without the requirement of maintaining a strict order of sequence. The drawings showing embodiments of the invention are semi-diagrammatic and not to scale and, particularly, some of the dimensions are for the clarity of presentation and are shown exaggerated in the drawing Figures. Similarly, although the views in the drawings for the ease of description generally show similar orientations, this depiction in the Figures is arbitrary for the most part. Generally, the invention can be operated in any orientation.

Notation and Nomenclature

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "processing" or "accessing" or "executing" or "storing" or "rendering" or the like, refer to the action and processes of a computer system, or similar electronic computing device, that manipulates and transforms data represented as physical (electronic) quantities within the computer system's registers and memories and other computer readable media into other data similarly represented as physical quantities within the computer system memories or registers or other such information storage, transmission or display devices. When a component appears in several embodiments, the use of the same reference numeral signifies that the component is the same component as illustrated in the original embodiment.

Energy Degrader for Radiation Therapy System

In practice, it has been observed that a particle beam may be preferentially scattered when it is incident on a surface with a shallow angle. Embodiment of the present disclosure employ an energy degrader including an emittance control material capable of preferentially scattering beam particles that are incident on a surface of the emittance control material with shallow angles toward a center line of the a particle beam, thereby enhancing forward scattering and suppressing the emittance growth of the particle beam as it transmits through the energy degrader.

Figure 2:
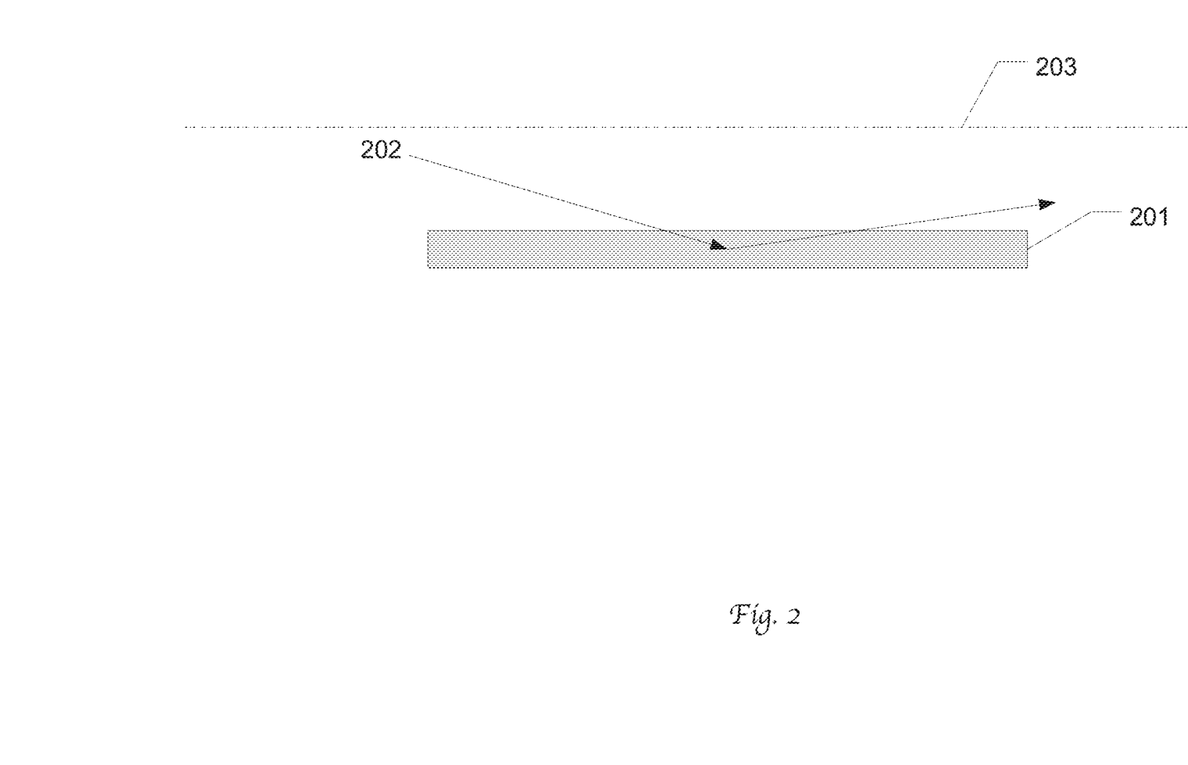
FIG. 2 illustrates the effect of preferential scattering of a beam particle that is incident on an emittance control material surface in a shallow angle in accordance with an embodiment of the present disclosure.

FIG. 2 illustrates the effect of preferential scattering of a beam particle 202 that is incident on an emittance control material surface in a shallow angle in accordance with an embodiment of the present disclosure. As will be described in greater details, the sheet of the emittance control material may be a portion of an energy degrader, e.g., an interface between the emittance control material and another material. The sheet is positioned in parallel with the center axis 203 of the particle beam as it enters the energy degrader. At the entrance of an energy degrader, the beam particle may travel along the direction of the center axis 203. Due to particle scattering by an energy attenuation material, e.g., a graphite material, the beam particle deviates from its original travel direction and impinges on the surface 201 in a shallow angle, as shown. The emittance control material surface 201 can serve to scatter back the particle toward its original travel direction 203.

Figure 3:
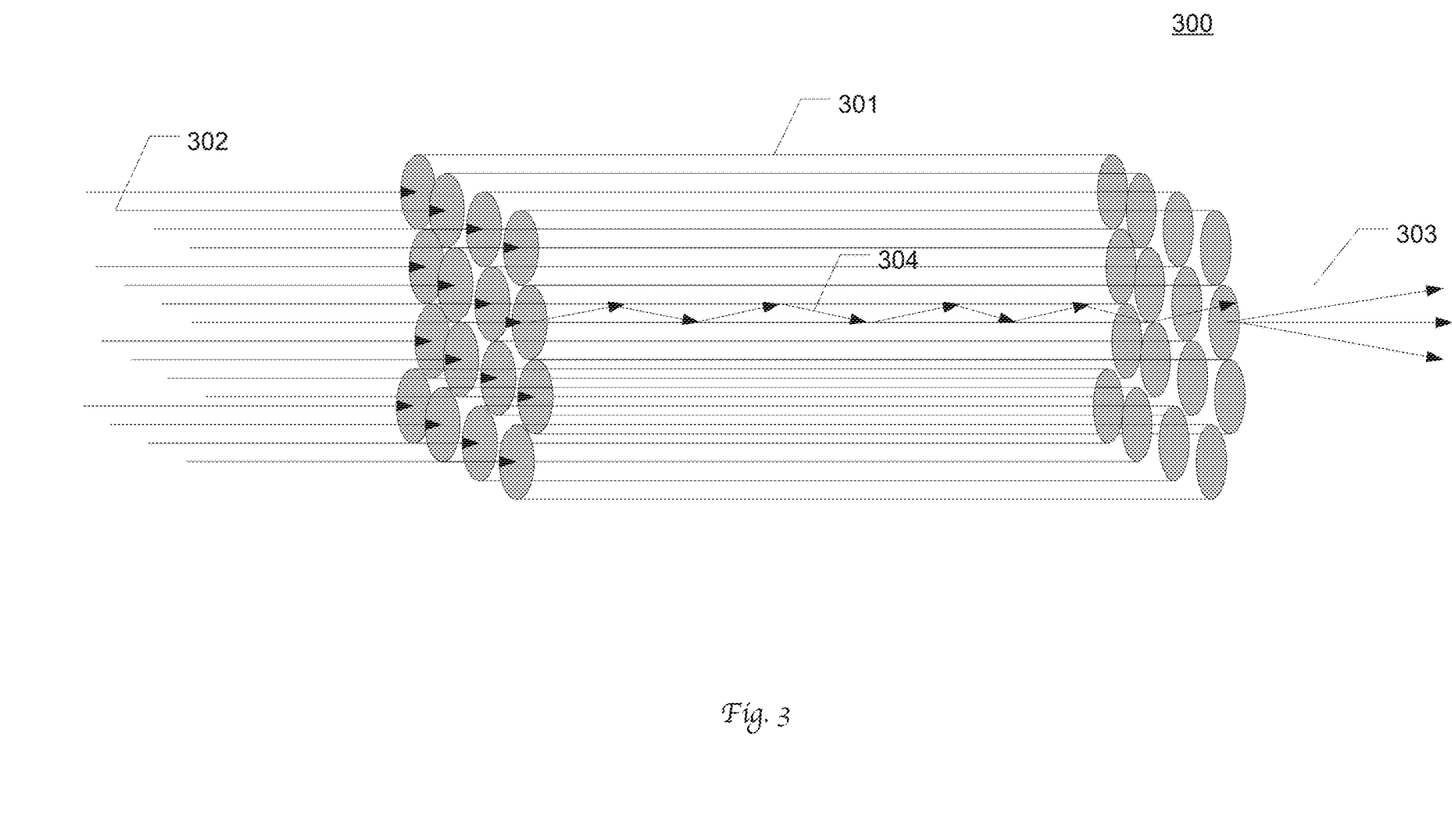
FIG. 3 illustrates an energy degrader made of carbon nanotubes used to attenuate the energy of a particle beam with limited emittance growth or without emittance growth.

In one approach, the emittance control material may be an engineered material having crystalline structure oriented in parallel with the beam center axis. FIG. 3 illustrates an energy degrader 300 made of carbon nanotubes 301 used to attenuate the energy of a particle beam 302 with limited emittance growth or without emittance growth. In the illustrated example, the carbon nanotubes 300 are oriented approximately parallel to the incident direction of the particle beam 302. For instance, a proton 304 enters the carbon nanotubes, and slows down as it is scattered by the atoms of a carbon nanotube, as shown by the arrowed trajectory line 304. As illustrated, the proton 304 impinges on the inside wall of the carbon nanotube in relatively shallow angles, and is reflected back towards the central beam axis by the nanotube wall due to preferential scattering. The proton can thus propagate through and exit the carbon nanotubes or the energy degrader 300 in a near-axis angle. This process may be analogous to light travelling in a fiber optic cable. Collectively, the proton beam 303 exiting the energy degrader can have a relatively narrow spatial emittance. This advantageously reduces of the number of particles removed from the beam by the collimator and thereby improves the particle transportation efficiency.

The present disclosure is not limited to any particular type of carbon nanotubes or any particular method of manufacturing the carbon nanotubes. For example, the carbon nanotubes used in an energy degrader may be single-walled nanotubes, multi-walled nanotubes, nanotori, nanobuds, graphenated carbon nanotubes, Nitrogen doped carbon nanotubes, and etc.

The carbon nanotubes can have any suitable geometric configuration as an energy degrader that is well known in the art. The present disclosure is not limited to any specific average length, material type, thickness, width or shape of the carbon nanotubes, or any specific placement of the energy degrader. Such an energy degrader may be used in conjunction with a suitable ESS collimator, or without the need for an ESS collimator.

In some embodiments, the energy degrader may be a variable energy degrader and includes multiple moveable pieces, e.g., wedges, the positions of which can be adjusted to vary the level of energy of the particle beams. In some embodiments, the energy degrader may be configured into an elongated cylindrical shape. In some embodiments, the energy degrader may be rotatable.

In another approach, an energy degrader may exploit a high-Z material as an emittance control material to enhance forward scattering of beam particles so as to realize energy range shifting without significant increase in emittance. As will be appreciated by those skilled in the art, the present disclosure is not limited to any specific type of high-Z material. To name a few, the high-Z material may be one or more of Tungsten, Lead, Tantalum, a compound thereof, and etc.

Figure 4A:
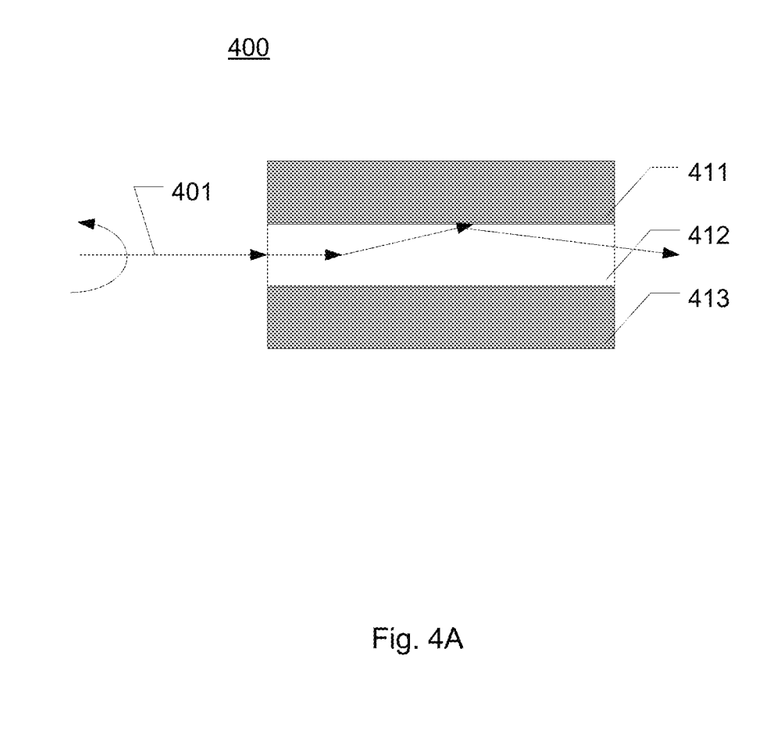
FIG. 4A illustrates a lateral view of an exemplary configuration of an energy degrader that utilizes a high-Z material to enhance forward scattering of the beam in accordance with an embodiment of the present disclosure.
Figure 4B:
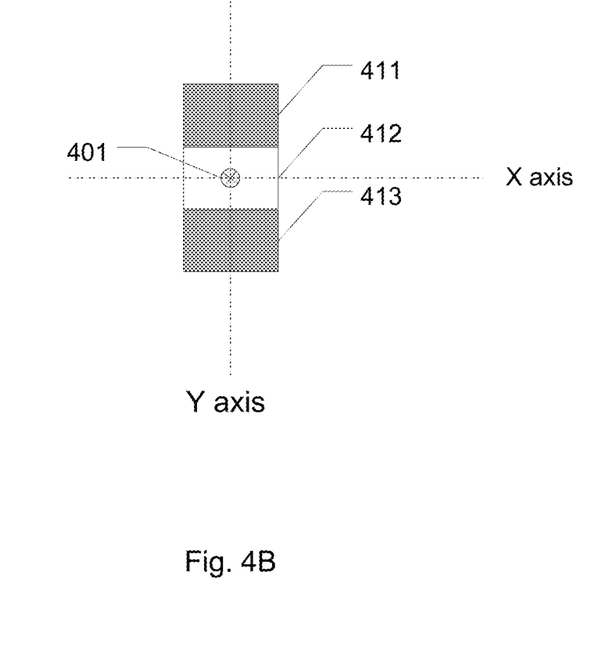
FIG. 4B illustrates a cross-section view of the exemplary configuration of the energy degrader as illustrated in FIG. 4A.

FIG. 4A illustrates a lateral view of an exemplary configuration of an energy degrader 400 that utilizes a high-Z material to enhance forward scattering of the beam in accordance with an embodiment of the present disclosure. The energy degrader 400 includes a three-layer sandwich structure including a low-Z material layer 412 primarily serving to attenuate the energy of the particle beam, and two high-Z material layers, 411 and 413, primarily serving to suppress the scattering caused by the low-Z material. The low-Z material may be at least one of Lithium, Beryllium, Carbon, Lexan, Water, Lucite, Al, or any other suitable material that is well known in the art. FIG. 4B illustrates a cross-section view of the exemplary configuration of the energy degrader 400 as illustrated in FIG. 4A.

For instance, as the trajectory line shows, a proton 401 entering the low-Z material layer 412 slows down through interactions with the atoms or molecules in the low-Z materials. When the proton strikes the interfaces of the low-Z and high-Z material, the proton may be reflected by the high Z material layer 411 back towards the beam axis direction for possibly multiple times until the proton exits the energy degrader 400. As a result, the beam emerging from the energy degrader can collectively present a limited spatial emittance growth.

In some embodiments, the energy degrader with a sandwich structure may be rotatable about the beam center axis to reduce the differences in beam emittance for the direction parallel to the sandwich structure ("X axis") and the direction perpendicular to the sandwich structure ("Y axis").

Figure 5A:
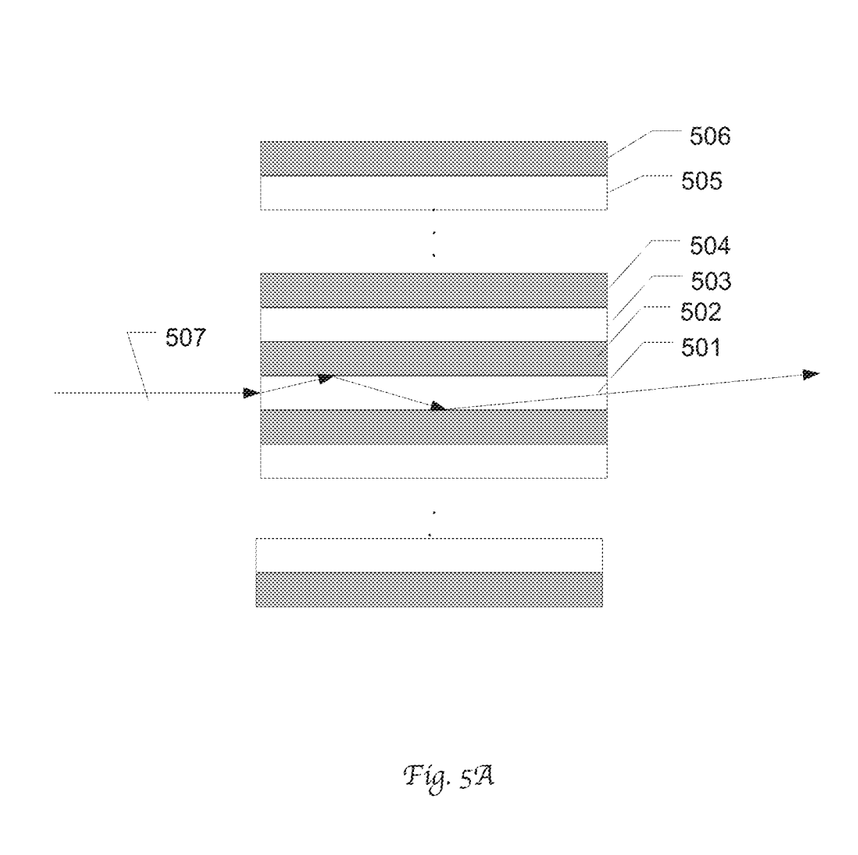
FIG. 5A illustrates an exemplary configuration of an energy degrader including a plurality of alternating layers made of high-Z material and low-Z material.

In some other embodiments, the energy degrader may be configured as a plurality of alternating layers made of the high-Z material and low-Z material. FIG. 5A illustrates an exemplary configuration of an energy degrader including a plurality of alternating layers made of high-Z material, e.g., 502, 504, and 506, and low-Z material, e.g., 501, 503, and 505. The cross sections of each layer may be in a rectangular shape or any other suitable shape that is well known in the art. The layers 501-506 in the stack may have equal or varying thicknesses, e.g., in the scale of approximately 1 mm. In some embodiments, the energy degrader includes 50 layers in total with 25 low-Z layers and 25 high-Z layers. In some embodiments, the stack is rotatable about a center axis of the particle beam 507. The stack of layers may be manufactured and processed in any process that is well known in the art.

Figure 5B:
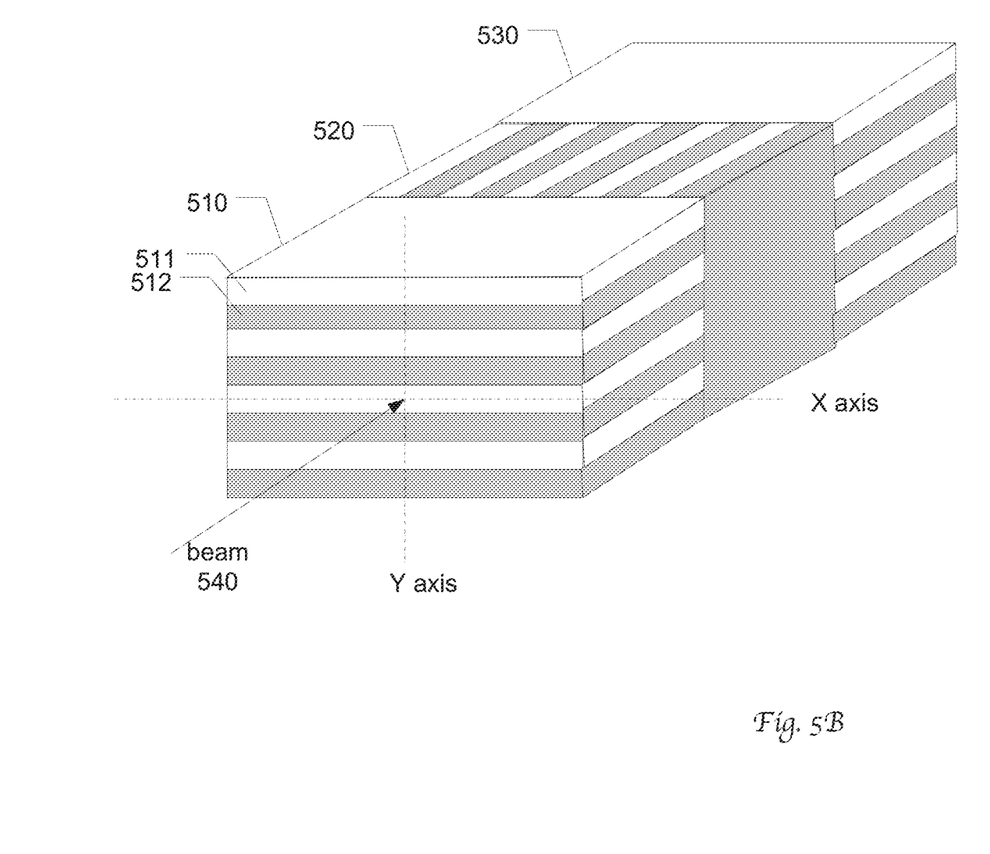
FIG. 5B illustrates an exemplary configuration of an energy degrader including a plurality of sections with each section having alternating layers made of high-Z material and low-Z material in accordance with an embodiment of the present disclosure.

FIG. 5B illustrates an exemplary configuration of an energy degrader including a plurality of sections, 510, 520 and 530 with each section having alternating layers made of high-Z material, e.g., 512, and low-Z material, e.g., 511, in accordance with an embodiment of the present disclosure. As illustrated, the layer stacks in the plurality of sections are positioned in different orientations. For example, the layers in section 510 and layers in section 520 are perpendicular to each other. As will be appreciated by those skilled in the art, the plurality of sections can be configured in any suitable geometric shape, dimensions, or orientations. For example, each section may be 1 mm along the incident direction of the beam 540.

Figure 6:
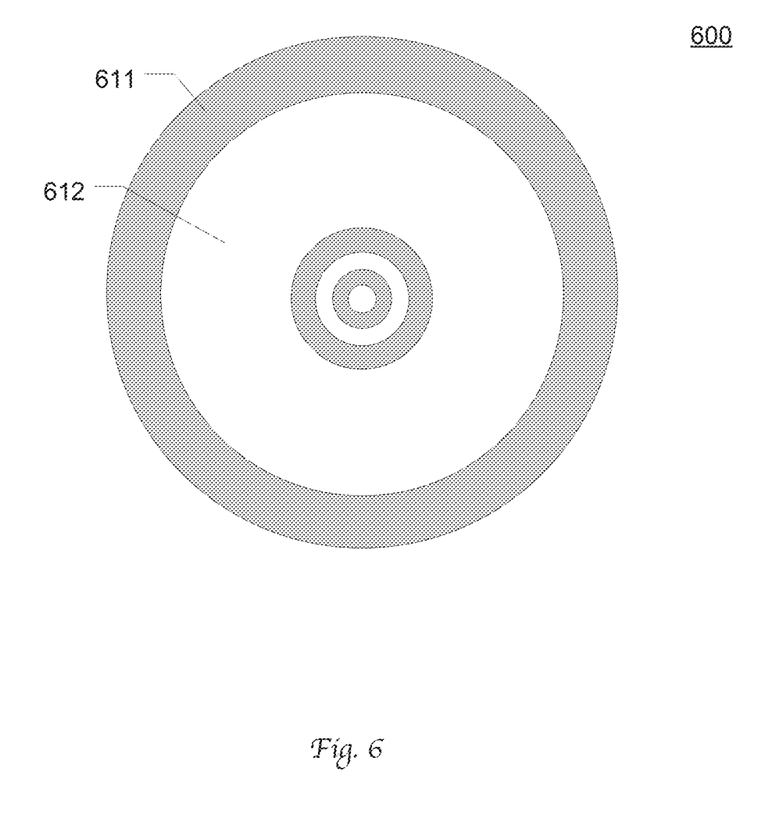
FIG. 6 illustrates an exemplary configuration of a cylindrical energy degrader including a plurality of alternating layers of high-Z material and low-Z material.

FIG. 6 illustrates an exemplary configuration of a cylindrical energy degrader 600 including a plurality of alternating layers of high-Z material, e.g., 612, and low-Z material, e.g., 611. The plurality of layers may have varying or equal thicknesses. The energy degrader 600 may comprise a plurality of moveable sections elongated along the incident beam direction, wherein the positions of the moveable sections may be varied depending on the prescribed level of energy to be delivered to the target. As will be appreciated by those skilled in the art, the plurality of sections can be configured in any suitable geometric shape, dimensions, or orientations.

Energy degraders in accordance with the present disclosure may be applied in any particle beam transportation line on any suitable equipment, including radiation therapy equipments. As will be appreciated by those skilled in the art, the energy attenuating material and the emittance control material used in an energy degrader may vary with the particle species in the particle beams. The energy degrader may be situated in a vacuum or in atmosphere.

Figure 7:
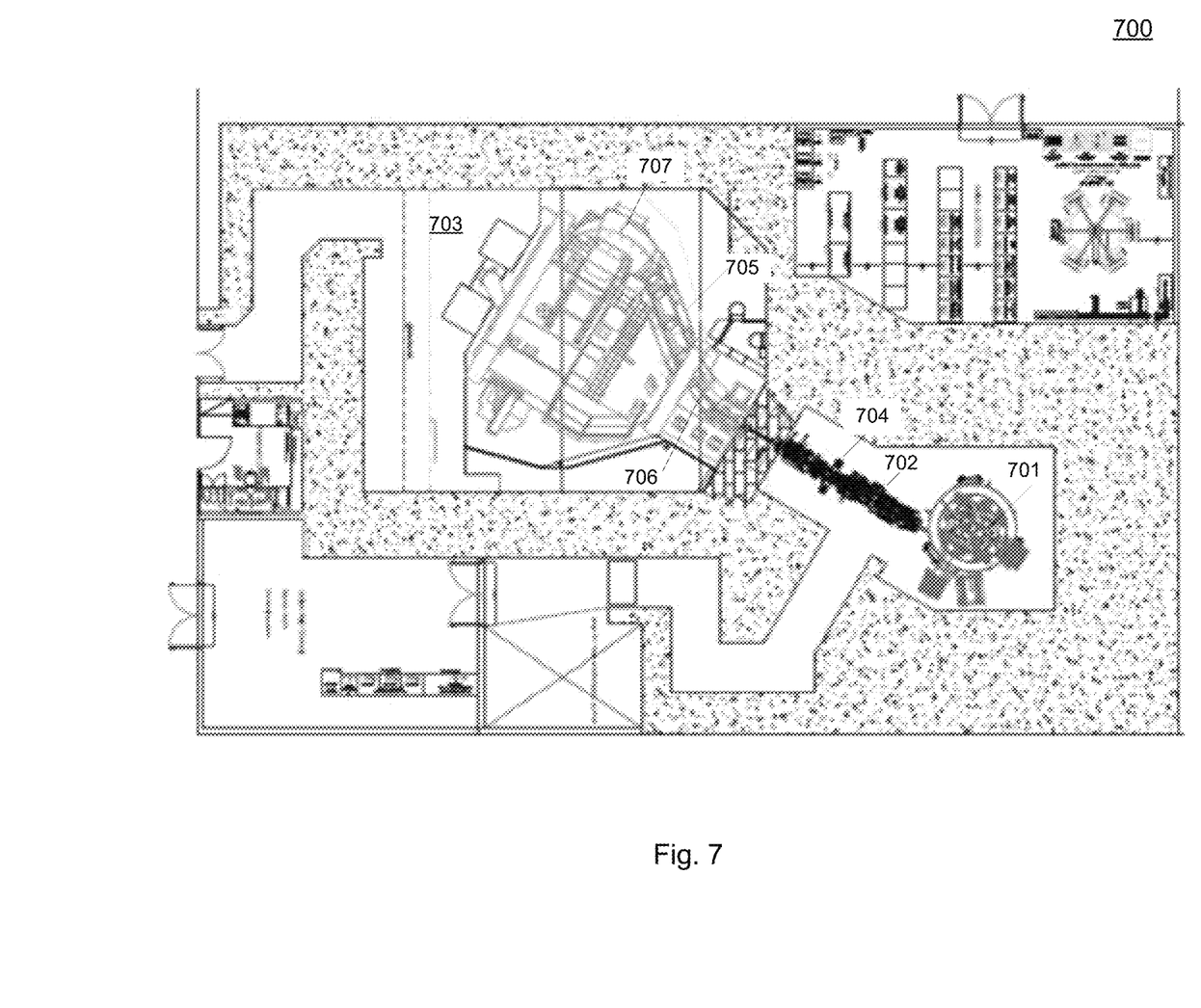
FIG. 7 illustrates an exemplary configuration of a medical facility equipped with an energy degrader in accordance with an embodiment of the present disclosure.

FIG. 7 illustrates an exemplary configuration of a medical facility 700 equipped with an energy degrader 704 in accordance with an embodiment of the present disclosure. The compact radiation system 700 is designed to deliver a proton beam from the stationary cyclotron 701 to an adjacent single treatment room 703. The proton radiation system 700 includes an accelerator 701, e.g. a cyclotron as shown, a short beam line 702 transporting the particle beam from the cyclotron 701 to the single treatment room 703 along a linear axis, an energy degrader 704 disposed in the beam line 702, a single set of dipole magnets 706 and 707, and a swiveling gantry 705 operable to deliver a proton beam to the treatment station through a nozzle in different angles. As described above, the energy degrader includes an emittance control material and can produce a beam with low emittance and thus high transportation efficiency.

In the single-room configuration 700, the cyclotron can be placed near the treat room as close as practically possible, and thus the beam line 704 can be short and linear, reducing the need for dipole magnets used for reorienting a particle beam. The system may further comprise a plurality of sets of focusing magnets mounted in the beam path to focus the particle team. In the illustrated embodiment, the dipole magnets 706 and 707 installed on the gantry 705 undertake the dual functions of energy selection as well as deflecting the particle beam from the beam line axis to the isocenter of the treatment station. In the illustrated embodiment, the 45° dipole magnet 706 located at the entry point of the gantry and the 135° dipole magnet 707 downstream can collectively bend the particle beam by 90° from the beam line 702 axis. At the same time, when the current in the coils of the magnets 706 and 707 is controlled to a precise current according to a target energy level, the magnets 706 and 707 in combination with a beam collimator are operable to perform the energy selection function.

An energy selection system (ESS) including an energy slits, bending magnets, and focusing magnets, can optionally be used to eliminate protons with excessive energy or deviations in angular direction. The proton beam is then provided to a treatment station via a beam transportation system. The beam transport system can tune and deliver the particle beam to a radiation station. At the end of the beam transport system, a gantry associated with a radiation nozzle delivers the beam onto an irradiation object, e.g. a tumor of a patient, in a fixed position supported by the irradiation station during operation. Similar systems can be used for other heavy particle radiation treatment, such as neutron, He or C ion beam.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A radiation therapy system, comprising:
   an accelerator operable to generate a particle beam;
   a beam line configured to transport said particle beam on a path from said accelerator to a gantry comprising a nozzle; and
   an energy degrader disposed in said beamline between said accelerator and said gantry, said energy degrader comprising:
      a plurality of sections including a first section, a second section, and a third section disposed successively in said path of said particle beam such that at least some particles of said particle beam pass into and through said first section and then into and through said second section and then into and through said third section, each section of said plurality of sections comprising a respective plurality of layers comprising a respective first layer, a respective second layer, and a respective third layer; wherein, in said each section, said respective first layer contacts said respective second layer and contacts said respective third layer and is sandwiched between said respective second layer and said respective third layer; wherein said layers in said first section are oriented at a right angle relative to said layers in said second section, and said layers in said second section are oriented at a right angle relative to said layers in said third section; wherein each layer of said respective plurality of layers in said first section is planar and has a uniform thickness throughout said each layer in said first section, each layer of said respective plurality of layers in said second section is planar and has a uniform thickness throughout said each layer in said second section, and each layer of said respective plurality of layers in said third section is planar and has a uniform thickness throughout said each layer in said third section; and wherein said each layer in said first section contacts said each layer in said second section and said each layer in said second section contacts said each layer in said third section;
   wherein, in said each section, each said respective first layer is made of a first material; and
   wherein, in said each section, each said respective second layer and each said respective third layer are made of materials that are different from said first material, wherein said materials that are different from said first material have a higher atomic number than said first material; wherein said first material has an atomic number that is high enough to attenuate energy of particles of said particle beam by virtue of particle scattering, wherein said atomic number of said first material is low enough to permit at least some of said particles to pass through said first material, wherein said particle scattering causes spatial emittance growth of said particle beam in said respective first layer and toward said respective second layer and said respective third layer, and wherein said materials that are different from said first material have an atomic number that is high enough to reflect at least some of said particles that are scattered by said first material from said respective second layer and said respective third layer back toward and into said respective first layer.

2. The radiation therapy system of claim 1, wherein said first material is selected from a group consisting of Lucite, graphite, Al, C, and Be, and wherein said second material is selected from a group consisting of W, Pb, and Ta.

3. The radiation therapy system of claim 1, wherein said energy degrader is rotatable.

4. The radiation therapy system of claim 1, wherein said particle beam comprises a beam selected from a group consisting of proton beam, neutron beam, electron beam, $He^{2+}$ beam, and $C^{6+}$ beam.

5. An energy degrader in a radiation therapy system, said energy degrader comprising:
   a plurality of sections including a first section, a second section, and a third section disposed successively in a path of a particle beam such that at least some particles of said particle beam pass into and through said first section and then into and through said second section and then into and through said third section, each section of said plurality of sections comprising a respective plurality of layers comprising a respective first layer, a respective second layer, and a respective third layer; wherein, in said each section, said respective first layer contacts said respective second layer and contacts said respective third layer and is sandwiched between said respective second layer and said respective third layer; wherein said layers in said first section are oriented at a right angle relative to said layers in said second section, and said layers in said second section are oriented at a right angle relative to said layers in said third section; wherein each layer of said respective plurality of layers in said first section is planar and has a uniform thickness throughout said each layer in said first section, each layer of said respective plurality of layers in said second section is planar and has a uniform thickness throughout said each layer in said second section, and each layer of said respective plurality of layers in said third section is planar and has a uniform thickness throughout said each layer in said third section; and wherein said each layer in said first section contacts said each layer in said second section and said each layer in said second section contacts said each layer in said third section;

wherein, in said each section, each said first respective layer is made of a first material;

wherein, in said each section, each said respective second layer and each said respective third layer are made of materials different from said first material, wherein said materials that are different from said first material have a higher atomic number than said first material;

wherein said particle beam enters said energy degrader from an accelerator and exits said degrader into a gantry comprising magnets, wherein said first material has an atomic number that is high enough to attenuate energy of particles of said particle beam by virtue of particle scattering, wherein said atomic number of said first material is low enough to permit at least some of said particles to pass through said first material; and wherein, in said each section, said particle scattering causes spatial emittance growth of said particle beam in said first respective layer and toward said respective second layer and said respective third layer, and wherein said materials that are different from said first material have an atomic number that is high enough to reflect at least some of said particles that are scattered by said first material from said respective second layer and said respective third layer back toward and into said respective first layer.

6. The energy degrader of claim 5 comprising a plurality of moveable members, wherein each moveable member comprises said first material and said second material.

7. The energy degrader of claim 5, wherein said first material is selected from a group consisting of Lucite, graphite, Al, C, and Be, and wherein said second material is selected from a group consisting of W, Pb and Ta.

8. The energy degrader of claim 5, wherein said particle beam comprises a beam selected from a group consisting of proton beam, neutron beam, electron beam, $He^{2+}$ beam, and $C^{6+}$ beam.

9. A system configured to generate a particle beam of a controlled energy, said system comprising:

a cyclotron configured to provide a particle beam;

a beam line assembly coupled to said cyclotron and operable to transport said particle beam on a path from said cyclotron to a gantry comprising a nozzle; and an energy degrader disposed in said beam line assembly between said cyclotron and said gantry, wherein said energy degrader comprises a plurality of sections including a first section, a second section, and a third section disposed successively in said path of said particle beam such that at least some particles of said particle beam pass into and through said first section and then into and through said second section and then into and through said third section, each section of said plurality of sections comprising a respective plurality of layers comprising a respective first layer, a respective second layer, and a respective third layer; wherein, in said each section, said respective first layer contacts said respective second layer and contacts said respective third layer and is sandwiched between said respective second layer and said respective third layer; wherein said layers in said first section are oriented at a right angle relative to said layers in said second section, and said layers in said second section are oriented at a right angle relative to said layers in said third section; wherein each layer of said respective plurality of layers in said first section is planar and has a uniform thickness throughout said each layer in said first section, each layer of said respective plurality of layers in said second section is planar and has a uniform thickness throughout said each layer in said second section, and each layer of said respective plurality of layers in said third section is planar and has a uniform thickness throughout said each layer in said third section; and wherein said each layer in said first section contacts said each layer in said second section and said each layer in said second section contacts said each layer in said third section;

wherein, in said each section, each said respective first layer is made of a first material; and wherein, in said each section, each said respective second layer and each said respective third layer are made of materials that are different from said first material, wherein said materials that are different from said first material have a higher atomic number than said first material; wherein said first material has an atomic number that is high enough to attenuate energy of particles of said particle beam by virtue of particle scattering, wherein said atomic number of said first material is low enough to permit at least some of said particles to pass through said first material, and wherein said particle scattering causes spatial emittance growth of said particle beam in said respective first layer and toward said respective second layer and said respective third layer, and wherein said materials that are different from said first material have an atomic number that is high enough to reflect at least some of said particles that are scattered by said first material from said respective second layer and said respective third layer back toward and into said respective first layer.

* * * * *